United States Patent [19]
Nitta et al.

[11] Patent Number: 5,488,138
[45] Date of Patent: Jan. 30, 1996

[54] PROCESS FOR PRODUCING HIGHLY PURE CARBOXYLIC ACID PHENYL ESTERS

[75] Inventors: Itaru Nitta, Tsukuba; Kuniaki Asai, Tondabayashi, both of Japan

[73] Assignee: Sumitomo Chemical Company, Limited, Osaka, Japan

[21] Appl. No.: 293,425

[22] Filed: Aug. 22, 1994

Related U.S. Application Data

[63] Continuation of Ser. No. 852,210, filed as PCT/JP91/01363, Oct. 7, 1991, abandoned.

[30] Foreign Application Priority Data

Oct. 8, 1990 [JP] Japan ................... 2-271012

[51] Int. Cl.$^6$ ................................. C07C 69/017
[52] U.S. Cl. ................................. 560/144
[58] Field of Search ................................. 560/144

[56] References Cited

U.S. PATENT DOCUMENTS

| | | | |
|---|---|---|---|
| 4,335,263 | 6/1982 | Minai | 568/437 |
| 4,814,110 | 3/1989 | Fong et al. | 260/400 |
| 4,933,489 | 6/1990 | Flynn | 560/139 |
| 4,964,870 | 10/1990 | Fong et al. | 8/111 |

FOREIGN PATENT DOCUMENTS

| | | |
|---|---|---|
| 0032153 | 7/1981 | European Pat. Off. . |
| 0184422 | 6/1986 | European Pat. Off. . |
| 1958954 | 5/1971 | Germany . |

OTHER PUBLICATIONS

Vol. 14, *Synthesis and Reaction of Organic Compounds II*, pp. 1014–1015, edited by Chemical Society of Japan, published on Dec. 20, 1977.

*Primary Examiner*—José G. Dees
*Assistant Examiner*—Samuel Barts
*Attorney, Agent, or Firm*—Stevens, Davis, Miller & Mosher

[57] ABSTRACT

The present invention provides a process for producing a carboxylic acid phenyl ester having such a high purity that is required in various fields.

A process for producing a highly pure carboxylic acid phenyl ester by reacting an aromatic hydroxy compound with a carboxylic acid anhydride, characterized by conducting the reaction in the presence of 0.01 part by weight or more of a tertiary amine per 100 parts by weight of the aromatic hydroxy compound.

6 Claims, No Drawings

PROCESS FOR PRODUCING HIGHLY PURE CARBOXYLIC ACID PHENYL ESTERS

This application is a continuation of U.S. application Ser. No. 07/852,210, filed as PCT/JP91/01363, Oct. 7, 1991, now abandoned.

TECHNICAL FIELD

The present invention relates to a process for producing carboxylic acid phenyl esters having such a high purity as required in various fields, which esters are suitably used as a monomer for synthesizing polymers and as a raw material for preparing pharmaceuticals and agricultural chemicals.

BACKGROUND ART

The technologies in such fields as electric, electronic, office automation (OA), audio-visual (AV), and automotive industries have been making remarkable progress in recent years. Polymeric materials used in such new fields are required to have meritorious properties such as high strength and high heat resistance. They have come to be required to have high level properties such as high dimensional accuracy, strength, rigidity, solder heat resistance and thin-wall processability by the advancement of reduction of the size and wall thickness particularly of electric parts such as relay parts, coil bobbins and connectors. As one of the polymeric materials which can satisfy the requirements, aromatic polyesters are suitably used. Among the aromatic polyesters, particularly liquid crystal polyesters showing anisotropy in molten state have desirable thin-wall processability and are rapidly coming into wide use as a material for electric parts.

Although acetylation method, phenyl esterification method and acid chloride method are known as the methods for producing aromatic polyesters, the liquid crystal polyesters showing anisotropy in molten state are mostly produced by acetylation method, in which polymerization is carried out by solution polymerization in a solvent having a high boiling point or by melt polymerization using substantially no solvent. In acetylation method, an aromatic hydroxy compound, one of the monomers, is converted into an acetic acid ester by the reaction between an aromatic hydroxy compound and acetic anhydride and the acetic acid ester is then polymerized by the intermolecular elimination of acetic acid. The conversion of an aromatic hydroxy compound into an acetic acid ester is generally conducted by adding acetic anhydride in an excess amount of about 1.1 moles per mole of the hydroxyl group and allowing the resulting mixture to react under reflux of acetic anhydride.

However, the preparation of acetic acid phenyl esters by the reaction between an aromatic hydroxy compound having the following formula (I) and acetic anhydride problematically accompanies the occurrence of side reactions such as the replacement of the hydrogen atom attached to the benzene nucleus by an acetyl group or the coloring of the reaction product at the later stage of reaction.

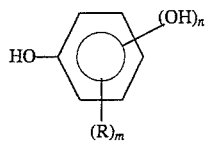
(I)

wherein R is halogen, alkyl having 1–5 carbon atoms or phenyl; and m and n are each an integer of 0–2, provided that when m is 2, two substituents represented by R may be different from each other.

Therefore, acetic acid phenyl esters used as the monomer for aromatic polyesters having a satisfactorily high purity cannot be obtained by the above-mentioned method. Acetylation method, when used for polymerizing an aromatic polyester having the corresponding repeating unit, cannot sufficiently raise the molecular weight of the resulting polymer nor prevent the coloring of the resulting polymer. Thus, by acetylation method, practically usable polymers are hardly obtained.

The same applies to the case where acetic anhydride is replaced by a carboxylic acid anhydride other than acetic anhydride.

DISCLOSURE OF THE INVENTION

In order to solve the above-mentioned problems, the present inventors have made extensive research for finding a catalyst which can give carboxylic acid phenyl esters in a high yield by the reaction between aromatic hydroxy compounds and carboxylic acid anhydrides. As the result, it has been found that tertiary amines act as a highly active catalyst for selectively forming carboxylic acid phenyl esters, that is, the presence of tertiary amines substantially prevents the formation of by-products during the reaction. The present invention has been attained on the basis of above finding.

The present invention relates to a process for producing a highly pure carboxylic acid phenyl ester by reacting an aromatic hydroxy compound having the formula (I) below with a carboxylic acid anhydride characterized in that the reaction is conducted in the presence of a tertiary amine in an amount of 0.01 part by weight or more per 100 parts by weight of the aromatic hydroxy compound.

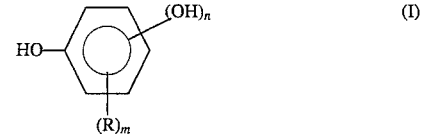
(I)

wherein R is halogen, alkyl having 1–5 carbon atoms, or phenyl; and m and n are each an integer of 0–2, provided that when m is 2, two substituents represented by R may be different from each other.

Representative choices from the aromatic hydroxy compounds are those having any one of the group of formulas (II).

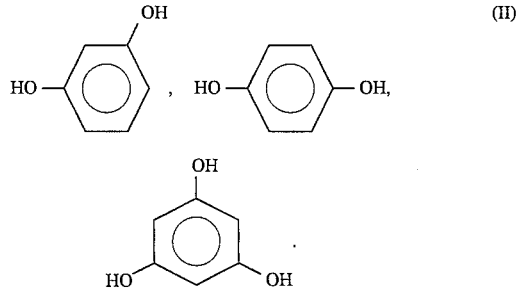
(II)

The carboxylic acid anhydrides include aliphatic, cyclic and aromatic carboxylic acid anhydrides.

Specific examples of the aliphatic carboxylic acid anhydrides are acetic anhydride, propionic anhydride, butyric anhydride, etc. Specific examples of the cyclic carboxylic acid anhydrides are succinic anhydride, maleic anhydride, etc. Specific examples of the aromatic carboxylic acid anhydrides are benzoic anhydride, toluic anhydride, naphthoic anhydride, etc.

Disclosed processes concerning the production of carboxylic acid phenyl esters from aromatic hydroxy compounds, particularly that of acetic acid phenyl esters, are classified into two groups. The process classified into the first group comprise the use of acid halides and an example of the acid halides is acetyl chloride. The processes classified into the second group comprise the use of acid anhydrides and an example of the acid anhydride is acetic anhydride. Of these, the processes of the second group are more advantageous than those of the first group, because the processes of the second group do not cause the problem of evolving corrosive chlorine gas. Therefore, the processes of the second group are mostly adopted to synthesize acetic acid phenyl esters for use as the monomer for preparing aromatic polyesters. In the processes of the second group, acetic anhydride is added to an aromatic hydroxy compound in an excess amount of about 1.1 moles per mole of hydroxyl groups and the resulting mixture is allowed to react under reflux of acetic anhydride for several hours.

The acetylation of resorcinol, an aromatic hydroxy compound represented by the formula (I), is so remarkably accelerated by concentrated sulfuric acid that the acetylation reaction proceeds exothermically in the presence of concentrated sulfuric acid. However, the reaction product thus obtained is colored red. And it gives a markedly colored polymer of low molecular weight by polymerization. The present inventors analyzed the reaction product by high performance liquid chromatography (HPLC) and nuclear magnetic resonance (NMR). Resultantly, it was found that the intended resorcinol diacetate was formed only in a yield of about 90% by mole and by-products such as resacetophenone resulting from acetylation of the hydrogen of benzene nucleus had been formed.

Accordingly, the present inventors have made extensive study on various catalysts with the aim of obtaining acetic acid phenyl esters of high purity in a high yield. As the result, it has been found that, surprisingly, tertiary amines typically represented by pyridine act as a highly active catalysts for selectively forming acetic acid phenyl esters, that is, the presence of tertiary amines in the reaction system substantially prevents the formation of by-products such as resacetophenone or the like.

Specific examples of the tertiary amines having a high catalytic activity and selectivity are pyridine, N,N-dimethylaniline, 4-dimethylaminopyridine, etc. Those having a high selectively and particularly preferred are pyridine and 4-dimethylaminopyridine. Those which are inexpensive, advantageous for industrial use and preferred are pyridine, triethylamine and N,N-dimethylaniline. Pyridine is particularly preferred.

Some prior art references disclose that resorcinol diacetate is a transparent, pale yellow liquid at ordinary temperature and ordinary pressure. However, according to the process of the present invention, resorcinol diacetate is obtained as a transparent colorless liquid at ordinary temperature and ordinary pressure. The present inventors have confirmed that tertiary amines have a similar effect also for other aromatic hydroxy compound such as phloroglucinol, etc.

The process for producing carboxylic acid phenyl esters of the present invention will be described in more detail. The description will be made using acetic anhydride as an example of carboxylic acid anhydrides. To an aromatic hydroxy compound represented by the formula (I) is added acetic anhydride in an amount of about 1.1 moles per mole of hydroxy groups, and the resulting mixture is stirred to dissolve the aromatic hydroxy compound in acetic anhydride. Then, a tertiary amine is added in an amount of not less than 0.01 part by weight, preferably 0.02–3 parts by weight, more preferably 0.03–2 parts by weight, relative to 100 parts by weight of the aromatic hydroxy compound.

When the amount of a tertiary amine added is less than 0.01 part by weight, the catalytic effect of the amine is insufficient. When the amount of a tertiary amine added is not less than 0.01 part by weight, the acetic acid phenyl ester obtained has a high purity, but when the amount is less than 0.1 part by weight, the resulting acetic acid phenyl ester is slightly colored. Thus, when a transparent, colorless acetic acid phenyl ester is intended, a tertiary amine should be added in an amount of not less than 0.1 part by weight.

On the other hand, the addition of a tertiary amine in an amount exceeding 3 parts by weight is economically disadvantageous.

After the addition of tertiary amine, the temperature of the reaction system is raised to initiate the reaction. The reaction temperature should be determined in consideration of the boiling point of the tertiary amine used and the reaction time. In the absence of a catalyst, the reflux temperature of acetic anhydride is usually used as the reaction temperature. However, when a tertiary amine is used as the catalyst, the reaction temperature, though depending also on the amount of the catalyst, may be the reflux temperature of acetic anhydride or below, preferably about 80° C. to about 145° C. (reflux temperature), and more preferably about 100° C. to about 145° C. (reflux temperature) in view of shortening the reaction time. Particularly preferred is the reflux temperature and its vicinity. The reaction time is preferably within about 1–3 hours. Under some reaction conditions, the reaction is sufficiently completed within about 1 hour. The purity of the acetic acid phenyl ester obtained can be confirmed by HPLC and NMR. The reaction is conducted in an inert gas atmosphere.

BEST MODE FOR CARRYING OUT THE INVENTION

The present invention will be described below with reference to Examples; however, it is not to be limited thereto. The analysis in the Examples were made in the following manner.

(1) High performance liquid chromatography (hereinafter HPLC): Determination was made by low pressure gradient method with a multi solvent delivery system 600 E (mfd. by Waters, Millipore Corp.) using as the mobile phase a methanol-acetic acid mixture (volume ratio: 1,000/5) and a water-acetic acid mixture (volume ratio: 1,000/5). The column used was an octadecylsilyl (ODS) column of 6.0 mm inside diameter and 15 cm length. Quantity determinations were made by the absolute calibration curve method, from which the conversion, selectivity and yield of respective reactions were calculated.

(2) Proton nuclear magnetic resonance spectroscopy (hereinafter 1H-NMR): Determination was made with a proton nuclear magnetic resonance spectroscope (200.133 MHz) (Type AC-200P, mfd. by Bulker Inc.) at room temperature using tetramethylsilane as the standard of chemical shift. The sample solution was prepared by dissolving 10 mg of a sample in 0.4 ml of deutero dimethyl sulfoxide.

(3) Flow temperature: This was determined with a Flow tester (Type CFT-500, mfd. by Shimadzu Corp.). A polymer sample was heat-melted at a temperature increasing rate of 4° C./min and then extruded through a nozzle of 1 mm inside diameter and 10 mm length under a load of 100 kg/cm². The temperature at which the polymer showed a melt viscosity of 48,000 poises was taken as the flow temperature.

(4) Lightness value (L) and hue values a (redness) and b (yellowness): The polymer sample was pulverized with a Bantam mill (mfd. by Hosokawa Micron Inc.) into particles of 300 μm or less. Sieving the particles with sieves of Tyler 60 mesh (246 μm opening) and Tyler 325 mesh (43 μm opening) gave powders of the maximum particle diameter of 246 μm or less and the minimum particle diameter of 43 μm or more.

The object color of the powder sample obtained was measured as its tristimulus values X, Y and Z with a colorimetric color-difference meter Z-1001DP (mfd. by Nippon Denshoku Kogyo Inc.) in accordance with the method 0° -d specified in JIS Z 8730, from which the lightness (L value), redness (a value) and yellowness (b value) were determined according to Hunter's color-difference equation specified in JIS Z 8730.

(5) Optical anisotropy: Optical anisotropy of a resin in molten state was examined by visual observation of a powdery polymer placed on a heating stage and heated at a rate of 10° C./min under polarized light. When the polymer does not melt completely in standing still, the observation was made under an applied pressure by using a spring pressure.

(6) Gel permeation chromatography (hereinafter GPC): Determination was made with a chromatographic apparatus (HLC-8020, mfd. by Tosoh Corp.) using a column of 7.8 mm inside diameter and 30 cm length and using a mixed solution of 2,3,5,6-tetrafluorophenol (hereinafter TFP) and chloroform (volume ratio of TFP/CHCl₃: 1/2.721) as the mobile phase. A 5 mg portion of a sample was dissolved in 5 ml of 2,3,5,6-tetrafluorophenol, then diluted with chloroform to twice the volume, prefiltered through a filter having a pore size of 0.45 μm and then subjected to the determination. The molecular weight was calculated by using a calibration curve based on standard polystyrenes.

(7) Solution viscosity: This was determined by using an Ubbelohde's viscometer and TFP as the solvent at 60° C.

(8) Properties of molded article: The bending strength and modulus of elasticity, and the heat distortion temperature (hereinafter HDT) were determined respectively in accordance with ASTM D-790 and ASTM D-648.

EXAMPLE 1

Acetylation of resorcinol-catalytic effect

In a 200-ml round-bottomed flask fitted with a crescent stirring blade, three-way cock and Dimroth condenser tube were placed 0.5 mole (55.0 g) of resorcinol and 1.1 moles (112.2 g) of acetic anhydride. The crescent stirring blade was rotated at 120 rpm and nitrogen was introduced through the three-way cock to replace the atmosphere is the system with nitrogen, whereby resorcinol was dissolved in the acetic anhydride. Thereafter, 275 mg (corresponding to 0.5 part by weight per 100 parts by weight of resorcinol) of pyridine was added as a tertiary amine. The flask was placed in an oil bath while cooling water was being passed through the Dimroth condenser tube. Then, the temperature of the oil bath was raised. The reactants were allowed to react for 1 hour while the inner temperature was maintained at 100° C.

The reaction product obtained was a transparent, colorless liquid at room temperature.

EXAMPLES 2 to 4

Three lots of acetic anhydride solution of resorcinol were prepared in the same manner as in Example 1. To each of the solutions was added, as a tertiary amine, triethylamine, N,N-dimethylaniline or 4-dimethylaminopyridine each in an amount of 275 mg (0.5 part by weight per 100 parts by weight of resorcinol). Then, resorcinol was reacted with acetic anhydride in the same manner as in Example 1. The resulting reaction products were all a transparent, colorless liquid at room temperature.

Comparative Example 1

An acetic anhydride solution of resorcinol was prepared in the same manner as in Example 1. The solution was heated without addition of a tertiary amine or such, and acetylation was carried out under reflux of acetic anhydride for 3 hours. The resulting reaction product was a transparent, orange liquid at room temperature.

Comparative Example 2

An acetic anhydride solution of resorcinol was prepared in the same manner as in Example 1, and one drop of concentrated sulfuric acid was added thereto. Resultantly, the reaction system evolved heat and the inner temperature rose up to 102° C. Thereafter, the flask was placed in an oil bath, and the reaction was conducted for 1 hour while the inner temperature was kept at 100° C. The reaction product obtained was a transparent, red liquid at room temperature.

The reaction products obtained above in Examples 1 to 4 and Comparative Examples 1 and 2 were analyzed by HPLC, and the conversion, selectivity and yield relating to resorcinol diacetate and the percentage of by-products formed were calculated. The results are shown in Table 1.

Table 1 reveals that in Examples 1 and 4, the conversion, selectivity and yield are all 100% and the percentage of by-products formed is 0%; in Examples 2 and 3, selectivity is 100%; and in all the Examples 1–4, utterly no by-product is formed.

Separately, the reaction products of Comparative Examples 1 and 2 were analyzed by NMR. Resultantly, it was found that most of the by-products are compounds having a resacetophenone structure produced by replacement of the hydrogen atom attached to the benzene nucleus by an acetyl group.

Comparative Example 3

Purification of resorcinol diacetate by vacuum distillation

Purification of the reaction product obtained in Comparative Example 1 by vacuum distillation was tried. First, acetic acid was distilled off by distillation under ordinary pressure. Then, the system was evacuated down to 10 mmHg, and vacuum distillation was conducted at a kettle temperature of 165° C. and a steam temperature of 155° C. The resorcinol diacetate thus obtained showed a purity of 98.6%. It reveals that it is impossible to prepare by vacuum distillation resorcinol diacetate having a purity required for use as the monomer for aromatic polyester.

EXAMPLE 5 and 6

Comparative Example 4

Acetylation of resorcinol—amount of catalyst added

The same reaction apparatus as in Example 1 was used. Four lots of acetic anhydride solution of resorcinol were prepared in the same manner as in Example 1. Then, pyridine was added as a tertiary amine to these solutions respectively in an amount of 0.005 part by weight (Comparative Example 4), 0.05 and 1.0 part by weight (Examples 5 and 6) per 100 parts by weight of resorcinol. The flask was placed in an oil bath and the reaction was conducted under the conditions shown in Table 2. The reaction products were analyzed by HPLC. The results are shown in Table 2.

There results reveal that when the amount of pyridine added is 0.005 parts by weight, the purity of the resorcinol diacetate obtained is insufficient although the catalytic effect of pyridine is recognized; when the amount is 0.01 part by weight or more, on the other hand, the resorcinol diacetate obtained has a high purity. Further, when combined with the results of Example 1, the results reveal that when the amount of pyridine added is less than 0.1 part by weight, the resulting resorcinol diacetate is slightly colored.

EXAMPLES 7 to 10

Comparative Example 5

Acetylation of various aromatic hydroxy compounds

In the same reaction apparatuses as used in Example 1 were placed 0.5 mole each of the aromatic hydroxy compounds shown in Table 3. Then, acetic anhydride was added thereto respectively in an amount of 1.1 moles per mole of hydroxyl groups. After 15 minutes of stirring, pyridine was added respectively in an amount of 0.5 part by weight per 100 parts by weight of the aromatic hydroxy compounds. Thereafter, the inner atmosphere of each of the flasks was replaced by nitrogen, the flask was placed in an oil bath while cooling water was being passed through the Dimroth condenser tube, and acetylation was conducted at a reaction temperature of 100° C. for 1 hour (Examples 7 to 10).

For comparison, an example wherein phloroglucinol was acetylated in the absence of catalyst is described below (Comparative Example 5). An acetic anhydride solution of phloroglucinol was prepared in the same manner as in Example 10. Then, without the addition of pyridine, the inner atmosphere of the flask was replaced with nitrogen, the flask was placed in an oil bath while cooling water was being passed through the Dimroth condenser tube, and acetylation was conducted at an oil bath temperature of 160° C. under reflux of acetic anhydride for 3 hours.

The reaction products obtained in Examples 7 to 10 and Comparative Example 5 were analyzed by HPLC, and the conversion, selectivity and yield relating to the corresponding acetic acid phenyl esters and the percentage of by-products formed were calculated. The results are shown in Table 3. It can be seen that pyridine is a catalyst having a high activity and selectivity in preparing acetic acid phenyl esters.

EXAMPLES 11, 12 and 13

Acetylation of resorcinol—amount of catalyst added

The same reaction apparatus as in Example 1 was used. Three lots of acetic anhydride solution of resorcinol were prepared in the same manner as in Example 1. Then, pyridine was added as a tertiary amine to these solutions respectively in an amount of 0.05, 0.1 and 0.5 part by weight (Examples 11, 12 and 13) per 100 parts by weight of resorcinol. The flask was placed in an oil bath, and the reaction was conducted under the conditions shown in Table 4. The reaction products were analyzed by HPLC. The results thus obtained are shown in Table 4.

Table 4 reveals that the addition of pyridine in an amount of 0.1 part by weight or more gave colorless and transparent resorcinol diacetate.

EXAMPLE 14

Acetylation of aromatic hydroxy compound

In the same apparatus as in Example 1 was placed 0.5 mole of phloroglucinol, and acetic anhydride was added thereto respectively in an amount of 1.1 moles per mole of hydroxyl groups. After 15 minutes of stirring, pyridine was added in an amount of 0.05 part by weight per 100 parts by weight of phloroglucinol. Thereafter, the inner atmosphere of the flask was replaced with nitrogen, the flask was placed in an oil bath while cooling water was being passed through the Dimroth condenser tube, and acetylation was conducted under reflux for 1 hour.

The reaction product obtained was analyzed by HPLC and the conversion, selectivity and yield relating to the reaction product and the percentage of by-products formed were calculated.

Resultantly, the conversion selectivity and yield were all 100% and the percentage of by-products formed was 0%. White crystals were obtained as the final product.

These results reveal that pyridine is a catalyst having a high activity and selectivity in preparing acetic acid phenyl esters.

Referential Examples 1 to 7

Comparative Referential Example 1

Aromatic polyester having resorcinol structure p-Hydroxybenzoic acid, terephthalic acid and resorcinol were placed in a polymerization vessel having an anchor-type stirrer so that the total amount of the three reactants was 12 moles and the molar ratio between them was varied as shown in Table 5. Then acetic anhydride was added thereto in an amount of 1.1 moles per mole of hydroxyl groups. After 15 minutes of stirring, pyridine was added thereto in an amount of 0.5 part by weight per 100 parts by weight of resorcinol. Thereafter, the atmosphere of the reaction system was thoroughly replaced with nitrogen, and acetylation was conducted at a reaction temperature of 100° C. for 1 hour.

Then, while the acetic acid formed was being distilled off, the temperature of the reaction mixture was raised at a temperature increasing rate of 1° C./min up to 270° C. The temperature was kept at the temperature for 90 minutes, and further raised at a temperature increasing rate of 1° C./min up to 300° C.

Then, polymerization at reduced pressure was conducted at 10 mmHg for 50 minutes in Referential Examples 1 to 3, and polymerization at normal pressure for 50 minutes in Referential Examples 4 to 7. The polymers thus obtained were pulverized with a Bantam mill (mfd. by Hosokawa Micron Inc.) into particles of 300 μm or less. In Referential Examples 4, 5 and 7, the particulate polymers were further subjected to solid phase polymerization in nitrogen atmosphere at 210° C. for 3 hours.

For comparison, hereinafter will be described a preparation example (Comparative Referential Example 1) of an aromatic polyester having a resorcinol structure in which the reactant composition is the same as in Referential Example 4 except for using no catalyst as pyridine, etc. Respective monomers were placed in the same reaction vessel as used in Referential Example 4 in a molar ratio shown in Table 5. Acetic anhydride was added thereto in an amount of 1.1 moles per mole of hydroxyl groups. While being stirred under nitrogen gas atmosphere, the reaction mixture was brought to elevated temperature. Then, the heater temperature was kept at 180° C. and acetylation was conducted under reflux for 3 hours. Thereafter, the reaction mixture was subjected to normal pressure polymerization and solid phase polymerization in the same manner as in Referential Example 4 to obtain a polymer.

Table 5 shows the results of analysis of the aromatic polyesters having a resorcinol structure obtained in Referential Examples 1 to 7 and Comparative Referential Example 1. Table 6 shows the properties of molded articles of the aromatic polyesters of Referential Examples 4 to 6 and Comparative Referential Example 1.

These results reveal that aromatic polyesters having a resorcinol structure prepared by using the highly pure resorcinol diacetate synthesized in the presence of tertiary amines are superior in heat resistance and mechanical properties and satisfactory in melt processability and color.

Further, it can be seen from Referential Example 7 that an aromatic polyester having a higher molecular weight can be obtained by using about 1.025 times the equivalent amount of resorcinol in the reaction.

Referential Examples 8 to 10

Aromatic polyester having resorcinol structure p-Hydroxybenzoic acid, terephthalic acid and resorcinol were placed in a polymerization vessel having an anchor-type stirrer so that the total amount of the three reactants was 12 moles and the molar ratio between them was varied as shown in Table 7. Then, acetic anhydride was added thereto in an amount of 1.1 moles per mole of hydroxyl groups. After 15 minutes of stirring, pyridine was added in an amount of 0.05 part by weight per 100 parts by weight of resorcinol. Thereafter, the atmosphere of the reaction system was thoroughly replaced with nitrogen, and acetylation was conducted under reflux for 1 hour.

Then, while the acetic acid formed was being distilled off, the temperature of the reaction mixture was raised at a temperature increasing rate of 1° C./min up to 270° C. The temperature was kept at the temperature for 90 minutes, and then further raised at a temperature increasing rate of 1° C./min up to 300° C.

Thereafter, polymerization at normal pressure was conducted for 50 minutes. The polymers thus obtained were pulverized with a Bantam mill (mfd. by Hosokawa Micron Inc.) into particles of 300 μm or less and, in Referential Examples 8 and 9, further subjected to solid phase polymerization in nitrogen atmosphere at 210° C. for 3 hours.

Table 7 shows the results of analysis of the aromatic polyesters obtained. Table 8 shows the properties of molded articles of the polyesters.

These results reveal that aromatic polyesters having a resorcinol structure prepared by using the highly pure resorcinol diacetate synthesized in the presence of a tertiary amine are superior in heat resistance and mechanical properties and satisfactory in melt processability and color.

TABLE 1

| | | Results of HPLC analysis (mol %) | | | | |
|---|---|---|---|---|---|---|
| | Catalyst | Conversion | Selectivity | Yield | By-product formed | Color |
| Comparative Example 1 | — | 100 | 90.0 | 90.0 | 9.8 | Orange, transparent |
| Comparative Example 2 | Conc. sulfuric acid | 100 | 93.1 | 93.1 | 6.6 | Red. transparent |
| Example 1 | Pyridine | 100 | 100 | 100 | 0 | Colorless, transparent |
| Example 2 | Triethylamine | 82.6 | 100 | 82.6 | 0 | Colorless, transparent |
| Example 3 | N,N-Dimethyl-aminopyridine | 78.4 | 100 | 78.4 | 0 | Colorless, transparent |
| Example 4 | 4-Dimethyl-aminopyridine | 100 | 100 | 100 | 0 | Colorless, transparent |

TABLE 2

| | Resorcinol (part by weight) | Pyridine (part by weight) | Reaction conditions | | Results of HPLC analysis (mol %) | | | |
|---|---|---|---|---|---|---|---|---|
| | | | Temperature (°C.) | Time (min) | Conversion | Selectivity | Yield | Color |
| Comparative Example 4 | 100 | 0.005 | 130 | 120 | 100 | 97.3 | 97.3 | Yellow, transparent |

TABLE 2-continued

|  | Resorcinol (part by weight) | Pyridine (part by weight) | Reaction conditions | | Results of HPLC analysis (mol %) | | | |
|---|---|---|---|---|---|---|---|---|
|  |  |  | Temperature (°C.) | Time (min) | Conversion | Selectivity | Yield | Color |
| Example 5 | 100 | 0.05 | 130 | 120 | 100 | 100 | 100 | Pale yellow, transparent |
| Example 6 | 100 | 1.0 | 100 | 60 | 100 | 100 | 100 | Colorless, transparent |

TABLE 3

|  | Aromatic hydroxy compound | Results of HPLC analysis (mol %) | | | | State of final product |
|---|---|---|---|---|---|---|
|  |  | Conversion | Selectivity | Yield | By-product formed | |
| Example 7 | Hydroquinone | 80.2 | 100 | 80.2 | 0 | White crystal |
| Example 8 | Methylhydroquinone | 82.2 | 100 | 82.2 | 0 | White crystal |
| Example 9 | Phenylhydroquinone | 84.9 | 100 | 84.9 | 0 | White crystal |
| Example 10 | Phloroglucinol | 100 | 100 | 100 | 0 | White crystal |
| Comparative Example 5 | Phloroglucinol | 80.7 | 12.3 | 9.93 | 87.5 | Orange liquid |

TABLE 4

|  | Resorcinol (part by weight) | Pyridine (part by weight) | Reaction conditions | | Results of HPLC analysis (mol %) | | | |
|---|---|---|---|---|---|---|---|---|
|  |  |  | Temperature (°C.) | Time (min) | Conversion | Selectivity | Yield | Color |
| Example 11 | 100 | 0.05 | Reflux temperature | 60 | 100 | 100 | 100 | Pale yellow, transparent |
| Example 12 | 100 | 0.1 | Reflux temperature | 60 | 100 | 100 | 100 | Colorless, transparent |
| Example 13 | 100 | 0.5 | Reflux temperature | 60 | 100 | 100 | 100 | Colorless, transparent |

TABLE 5

|  | Molar ratio of reactants p-Hydroxybenzoic acid/Terephthalic acid/Resorcinol | Flow temperature (°C.) | GPC | | | Lightness, hue | | | Liquid crystallinity in molten state |
|---|---|---|---|---|---|---|---|---|---|
|  |  |  | Number average molecular weight (Mn) | Weight average molecular weight (Mw) | Mw/Mn | L | a | b | |
| Referential Example 1 | 0/100/100 | 262 | $1.43 \times 10^4$ | $3.39 \times 10^4$ | 2.37 | 83 | 1.1 | 19.8 | Not observed |
| Referential Example 2 | 100/100/100 | 231 | $1.18 \times 10^4$ | $3.01 \times 10^4$ | 2.55 | 83 | 1.0 | 19.8 | Not observed |
| Referential Example 3 | 200/100/100 | 244 | $1.55 \times 10^4$ | $4.77 \times 10^4$ | 3.08 | 84 | 0.9 | 19.8 | Not observed |

TABLE 5-continued

| | Molar ratio of reactants p-Hydroxybenzoic acid/Terephthalic acid/Resorcinol | Flow temperature (°C.) | GPC Number average molecular weight (Mn) | GPC Weight average molecular weight (Mw) | Mw/Mn | Lightness, hue L | Lightness, hue a | Lightness, hue b | Liquid crystallinity in molten state |
|---|---|---|---|---|---|---|---|---|---|
| Referential Example 4 | 350/100/100 | 259 | $1.87 \times 10^4$ | $5.30 \times 10^4$ | 2.84 | 85 | 0.9 | 19.7 | Observed |
| Referential Example 5 | 450/100/100 | 261 | $9.44 \times 10^3$ | $2.71 \times 10^4$ | 2.87 | 87 | 0.9 | 19.7 | Observed |
| Referential Example 6 | 800/100/100 | 309 | Insoluble in solvent | | | 88 | 0.9 | 19.7 | Observed |
| Referential Example 7 | 350/100/102.5 | 276 | $2.00 \times 10^4$ | $6.67 \times 10^4$ | 3.34 | 84 | 0.9 | 19.8 | Observed |
| Comparative Referential Example 1 | 350/100/100 | 223 | $9.98 \times 10^3$ | $2.50 \times 10^4$ | 2.51 | 61 | 7.6 | 22.6 | Unable to be determined owing to dark color |

TABLE 6

| | Molding temperature (°C.) | HDT (°C.) | Bending strength (kgf/cm$^2$) | Flexural modulus (kgf/cm$^2$) |
|---|---|---|---|---|
| Referential Example 4 | 300 | 166 | 1060 | 32200 |
| Referential Example 5 | 300 | 167 | 790 | 38000 |
| Referential Example 6 | 370 | 207 | 700 | 72000 |
| Comparative Referential Example 1 | 300 | 151 | 660 | 29900 |

TABLE 7

| | Molar ratio of reactants p-HBA*$^{1)}$/ TPA*$^{2)}$/ Resorcinol | Flow temperature (°C.) | GPC Number average molecular weight (Mn) | GPC Weight average molecular weight (Mw) | Mw/Mn | Lightness, hue L | Lightness, hue a | Lightness, hue b | Liquid crystallinity in molten state |
|---|---|---|---|---|---|---|---|---|---|
| Referential Example 8 | 350/100/100 | 261 | $1.90 \times 10^4$ | $5.51 \times 10^4$ | 2.90 | 83 | 1.0 | 19.7 | Observed |
| Referential Example 9 | 450/100/100 | 260 | $9.03 \times 10^3$ | $2.66 \times 10^4$ | 2.95 | 86 | 0.9 | 19.7 | Observed |
| Referential Example 10 | 800/100/100 | 310 | Insoluble in solvent | | | 86 | 0.9 | 19.7 | Observed |

Notes:
*$^{1)}$p-Hydroxybenzoic acid
*$^{2)}$Terephthalic acid

TABLE 8

| | Molding temperature (°C.) | HDT (°C.) | Bending strength (kgf/cm$^2$) | Flexural modulus (kgf/cm$^2$) |
|---|---|---|---|---|
| Referential Example 8 | 300 | 165 | 1040 | 32200 |
| Referential Example 9 | 300 | 168 | 780 | 38100 |
| Referential Example 10 | 370 | 207 | 720 | 73000 |

Industrial Applicability

Carboxylic acid phenyl esters of high purity can be provided under milder conditions than before by reacting an aromatic hydroxy compound with a carboxylic acid anhydride in the presence of a tertiary amine such as pyridine and the like. The carboxylic acid phenyl esters thus obtained are suitably used as a monomer for preparing aromatic polyesters. They further can be used as a raw material for preparing pharmaceuticals and agricultural chemicals.

In particular, resorcinols are a monomer having meta-orienting property and are of great interest in having such a property that the use thereof as a monomer for preparing aromatic polyesters of high crystality efficiently reduces the melting point of the resulting polyesters and markedly improves the processability of the resulting polyesters. However, in the absence of a catalyst, the reaction between resorcinols and acetic anhydride gave resorcinol diacetates of low purity. Therefore, it was impossible to produce aromatic polyesters having a resorcinol skeleton from the corresponding resorcinol diacetates by acetylation method, although good physical properties can be expected for such polyesters.

However, as shown in the disclosure of the present invention, resorcinol diacetates of high purity can be obtained by reacting resorcinols and acetic anhydride in the presence of a tertiary amine. Consequently, the polymerization using such highly pure resorcinol diacetates gives aromatic polyesters superior in heat-resistance, mechanical properties, melt processability and color tone, and thus the aromatic polyesters are of great industrial value.

We claim:

1. A process for producing a highly pure carboxylic acid phenyl ester by reacting an aromatic hydroxy compound having the formula (I),

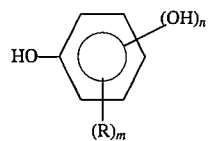

wherein R is halogen, alkyl having 1–5 carbon atoms, or phenyl; and m and n are each an integer of 0–2, provided that when m is 2, two substituents represented by R may be different from each other, with a carboxylic acid anhydride, characterized by conducting the reaction in the presence of 0.02 to 3 parts by weight of a tertiary amine per 100 parts by weight of the aromatic hydroxy compound.

2. A process for producing a highly pure carboxylic acid phenyl ester according to claim 1, wherein the carboxylic acid anhydride is acetic anhydride.

3. A process for producing a highly pure carboxylic acid phenyl ester according to claim 1, characterized in that the tertiary amine is at least one member selected from the group consisting of pyridine, triethylamine, N,N-dimethylaniline and 4-dimethylaminopyridine.

4. A process for producing a highly pure carboxylic acid phenyl ester according to claim 1, wherein the tertiary amine is pyridine.

5. A process for producing a highly pure carboxylic acid phenyl ester according to claim 1, characterized in that the aromatic hydroxy compound is at least one compound having any one of the group of formulas (II),

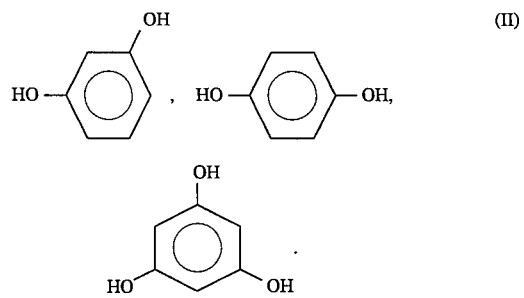

6. A process for producing a highly pure carboxylic acid phenyl ester according to claim 1, wherein the aromatic hydroxy compound is resorcinol.

* * * * *